(12) United States Patent
Chung et al.

(10) Patent No.: US 7,935,763 B2
(45) Date of Patent: *May 3, 2011

(54) THERMOPLASTIC VULCANIZATE COMPOSITIONS HAVING IMPROVED EXTRUSION PERFORMANCE AND METHODS OF FORMATION THEREOF

(75) Inventors: Oansuk Chung, Houston, TX (US); Trazollah Ouhadi, Liege (BE); Eugene R. Uhl, Massillon, OH (US)

(73) Assignee: ExxonMobil Chemical Patents Inc., Houston, TX (US)

( * ) Notice: Subject to any disclaimer, the term of this patent is extended or adjusted under 35 U.S.C. 154(b) by 677 days.

This patent is subject to a terminal disclaimer.

(21) Appl. No.: 11/546,076

(22) Filed: Oct. 11, 2006

(65) Prior Publication Data

US 2007/0037931 A1    Feb. 15, 2007

(51) Int. Cl.
*C08F 8/00* (2006.01)
*C08L 23/00* (2006.01)
*C08L 23/04* (2006.01)

(52) U.S. Cl. ........ 525/193; 525/191; 525/192; 525/240; 525/232; 525/194; 524/120

(58) Field of Classification Search .................. 525/192, 525/210, 240, 191, 232, 193, 194; 524/120
See application file for complete search history.

(56) References Cited

U.S. PATENT DOCUMENTS

| | | | | |
|---|---|---|---|---|
| 3,806,558 A | * | 4/1974 | Fischer | 525/198 |
| 4,130,535 A | * | 12/1978 | Coran et al. | 524/487 |
| 4,311,628 A | | 1/1982 | Abdou-Sabet et al. | |
| 5,100,947 A | | 3/1992 | Puydak et al. | |
| 5,157,081 A | | 10/1992 | Puydak et al. | |
| 5,286,795 A | * | 2/1994 | Ainsworth | 525/195 |
| 5,552,482 A | | 9/1996 | Berta | |
| 6,255,389 B1 | * | 7/2001 | Ouhadi et al. | 525/76 |
| 6,586,507 B2 | * | 7/2003 | Galbo et al. | 524/102 |
| 6,720,376 B2 | * | 4/2004 | Itoh et al. | 524/352 |
| 2005/0288434 A1 | * | 12/2005 | Sugiura et al. | 525/70 |
| 2006/0178478 A1 | * | 8/2006 | Ellul | 525/191 |

FOREIGN PATENT DOCUMENTS

| | | |
|---|---|---|
| EP | 0 487 077 | 5/1992 |
| EP | 0 911 364 | 4/1999 |
| EP | 1 550 693 | 7/2005 |
| JP | 08 183889 | 7/1996 |
| JP | 08183889 * | 7/1996 |
| JP | 11 012409 | 1/1999 |
| JP | 11012409 * | 1/1999 |
| WO | WO 86/02088 | 4/1986 |
| WO | WO 99/24506 | 5/1999 |

OTHER PUBLICATIONS

Jessie D. Gander and A. Jeffrey Giacomin, Review of Die Lip Buildup Thermoplastics Extrusion, 37(7), *Polymer Engineering and Science*, Jul. 1997.

T. Sun et al., "*Effect of Short Chain Branching on the Coil Dimensions of Polyolefins in Dilute Solution*", Macromolecules, 2001, vol. 34, pp. 6812-6820.

M. Ellul et al., "*Crosslink Densities and Phase Morphologies in Dynamically Vulcanized TPEs*", Rubber Chemistry and Technology, 1995, vol. 68, pp. 573-584.

* cited by examiner

*Primary Examiner* — Vasu Jagannathan
*Assistant Examiner* — Irina Krylova

(57) ABSTRACT

In one embodiment is a thermoplastic vulcanizates having improved extrusion properties formed from a composition that includes from 20% to about 80% by weight of an elastomer, from about 80% to about 20% by weight of a thermoplastic, from about 0.05 to about 12 phr of a multifunctional methacrylate monomer peroxide curing coagent; and from about 0.02 to about 6 phr of a phosphorous containing stabilizer. The resultant thermoplastic vulcanizate may be cured with a peroxide curing agent and shows improved die lip build up compared to conventionally prepared thermoplastic vulcanizates. Methods of forming thermoplastic vulcanizates having improved die lip build up are also taught.

13 Claims, No Drawings

THERMOPLASTIC VULCANIZATE COMPOSITIONS HAVING IMPROVED EXTRUSION PERFORMANCE AND METHODS OF FORMATION THEREOF

I. BACKGROUND OF THE INVENTION

A. Field of Invention

The present invention relates to compositions for forming thermoplastic vulcanizates and methods of forming thermoplastic vulcanizates to improve extrusion properties.

B. Description of the Related Art

Thermoplastic vulcanizates ("TPV") are vulcanized compositions that include a large amount of finely dispersed crosslinked elastomer particles in a continuous thermoplastic. TPVs are vulcanized by a process called dynamic vulcanization—a process of selectively crosslinking the elastomer component during its melt mixing with the molten thermoplastic. TPVs have the benefit of the elastomeric properties provided by the elastomer phase, with the processability of thermoplastics.

TPVs are routinely used in the manufacture of a variety of products, the form of which is created by means of extruding the molten TPV through a die, wherein the die is shaped to impart the desired form to the extrusion. One common problem that arises in this extrusion process is that as the TPV material passes through the die, material deposits form on the outer lip of the die. The deposits form what are commonly referred to as a "moustache" on the die lip, or "die-lip buildup".

While the specific causes of die lip buildup during the TPV extrusion process are widely discussed and disputed, it is undisputed that die lip buildup poses a significant problem for extruders. An effort to describe the causes of die lip buildup in conventional thermoplastic extrusion is made by Jessie D. Gander and A. Jeffrey Giacomin in "Review of Die Lip Buildup in thermoplastics Extrusion" 37(7)POLYMER ENGINEERING AND SCIENCE (July-1997). Though this reference refers to thermoplastics extrusion, it is believed to be an apt reference with respect to the cause of die lip buildup in thermoplastic vulcanizate extrusion. The shape, and more specifically, the consistency of the shape, imparted to the molten TPV as it passes through the extruder die is dependant on the smoothness of the die at its mouth. The presence of material deposits or buildup at the mouth of the extruder die can affect the shape of the die mouth. Additionally, deposits may impart unwanted grooves on the extrusion as the deposit digs into the surface of the molten extrusion. Finally, deposits may, from time to time, slough off of the die lip and onto the TPV extrusion, creating an unwanted bead or glob on the extrusion.

As a result of die lip buildup, it may be necessary to periodically shut down the extrusion line in order to manually remove the deposits. This is highly undesirable. Alternatively, or additionally, it may be necessary to discard portions of the extrusion that have been marred by the buildup. This can result in material waste, increased manufacturing time, increased cost, and lower overall quality.

Methods to reduce die lip buildup have generally produced unsatisfactory results, either in the total reduction of die lip buildup, or in the overall physical properties of the resultant TPV. Two approaches are described in EP 0 911 364 and EP 1 550 693. In the first reference, a process for making a TPV is described that involves adding a portion of the total polyolefin thermoplastic to the TPV composition after the elastomer curing agent has been added to the extrusion chamber and the elastomer has been substantially cured. This approach to reducing die lip deposits would appear to be predicated on the theory that protecting a portion of the thermoplastic from degradation by the peroxide curing agent, by adding a portion of the thermoplastic after the curing agent has been depleted in vulcanizing the constituent elastomer, will result in improved TPV physical characteristics that lead to reduced buildup on later extrusion. However, the reduction resulting from this method is not satisfactory. In the latter reference (EP 1 550 693), syndiotactic polypropylene is substituted for isotactic polypropylene as the preferred polyolefin thermoplastic. While reduced die buildup is claimed, the resultant TPV has poor compression data at the extrusion temperature.

It would be desirable to provide TPV compositions and methods of forming thermoplastic vulcanizates that result in a reduction of die lip buildup as compared to conventionally formed TPVs while maintaining other physical properties.

II. SUMMARY OF THE INVENTION

One aspect of the invention is directed to a peroxide-cured thermoplastic vulcanizate composition comprising from 20 to 80% by weight of an at least partially cured elastomer and from 80 to 20% by weight of a thermoplastic; wherein the thermoplastic vulcanizate is cured in the presence of at least one multifunctional methacrylate coagent and at least one phosphorus containing stabilizer.

In another embodiment, the thermoplastic vulcanizate is cured in the presence of from about 0.05 to about 12 phr of a multifunctional methacrylate coagent and from about 0.02 to about 8 phr of a phosphorus containing stabilizer.

In yet another embodiment, the thermoplastic vulcanizate is cured in the presence of from about 1 to about 10 phr of a multifunctional methacrylate coagent and from about 0.2 to about 6 phr of a phosphorus containing stabilizer.

Another aspect of the invention is directed to a method of forming a thermoplastic vulcanizate comprising the steps of melt blending from 20 to 80% by weight of at least one elastomer and from 80 to 20% by weight of a thermoplastic in the presence of from about 0.05 to about 10 phr of a peroxide curing agent; from about 0.05 about 12 phr of a multifunctional methacrylate coagent; from about 0.02 to about 6 phr of a phosphorus containing stabilizer.

In another embodiment of the method, the melt blend is extruded from an extruder, the resulting extrudate not showing die-lip buildup at 5 minutes.

In another embodiment, the phosphorus containing stabilizer is selected from the group consisting of phosphates, phosphonites and blends thereof.

In yet another embodiment, the chamber is a twin screw extruder.

Other aspects and embodiments of the methods and compositions of the subject invention may be described herein.

III. DESCRIPTION OF THE PREFERRED EMBODIMENT

According to one embodiment of the present invention, which will be elucidated in further variants and embodiments described below, there is taught a thermoplastic vulcanizate composition that comprises an elastomer, a thermoplastic, a curing agent, which is preferably a peroxide curing agent, a peroxide curing coagent, and a phosphorous containing stabilizer. In the exemplary composition, the elastomer is present in amounts from about 20 to about 80% by weight of the total elastomer plus thermoplastic, and the thermoplastic is present in an amount from about 80% to about 20% by weight of the total elastomer plus thermoplastic. For purposes herein, the terms "% by weight" and "wt. %" are used interchangeably. The peroxide curing agent may be present in amounts from about 0.05 to about 10 phr in one embodiment. The peroxide curing coagent may be present in amounts from about 0.05 to about 12 phr in one embodiment. The phosphorous containing stabilizer may be present in amounts from about 0.02 to about 6 phr in one embodiment. A fully cured thermoplastic vulcanizate may be formed as the product of melt blending the elastomer, the thermoplastic, the peroxide curing agent and coagent, and the phosphorous containing stabilizer. On extrusion of the fully cured TPV, under conditions specified according to the exemplary testing method, which is described in detail below, the time to first visible material buildup on the die lip is greater than about 5 minutes and, preferably, 15 minutes, and in another embodiment, the time to slough (material drip) is greater than about 15 minutes, and, preferably, 30 minutes.

Once cured, the thusly prepared thermoplastic vulcanizate can be referred to as a "peroxide-cured" thermoplastic vulcanizate composition comprising from 20 to 80% by weight of an at least partially cured elastomer and from 80 to 20% by weight of a thermoplastic; wherein the thermoplastic vulcanizate has been cured in the presence of at least one multifunctional methacrylate coagent and at least one phosphorus containing stabilizer. The thermoplastic vulcanizate is thus cross-linked and includes the peroxide/co-agent induced crosslinking and side products, as well as the stabilizer and any side-products resulting from the vulcanization process.

Another aspect of the invention is directed to a method of preparing a partially or fully cured TPV, which, on extrusion under conditions specified according to the exemplary testing method, demonstrates a time to first visible material buildup on the die lip that is greater than about 5 minutes, comprising the step of melt blending from about 20% to about 80% by weight of an elastomer, from about 80% to about 20% by weight of a thermoplastic, from about 0.05 phr to about 10 phr of a peroxide curing agent, from about 0.05 phr to about 12 phr of a multifunctional methacrylate monomer coagent ("MMMC") and from about 0.02 phr to about 6 phr of a phosphorous containing stabilizer, in a chamber, the chamber preferably being multi-screw extruder.

Having generally described the exemplary compositions and methods, each will be further elucidated.

In one embodiment, the TPV composition may comprise from about 20% to about 80% elastomer by weight of TPV composition, and from about 30% to about 70% by weight in another embodiment, and in another embodiment from about 35% to about 65% by weight, and in yet another embodiment, from about 40% to about 60% by weight of a elastomer, which may comprise one or more than one elastomer(s). When referring to the "elastomer" or "thermoplastic", the term "% by weight" or "wt. %" is used with respect to the total of the elastomer plus thermoplastic in the TPV composition.

The term "elastomer" refers to any natural or synthetic polymer which can be vulcanized or cured so as to exhibit elastomeric properties. Exemplary elastomers for use in accordance with the present invention may include unsaturated non-polar elastomers, monoolefin copolymer elastomers comprising non-polar, elastomer copolymers of two or more monoolefins (EP elastomer), which may be copolymerized with at least one polyene, usually a diene (EPDM elastomer). EPDM (ethylene-propylene-diene elastomer) is a polymer of ethylene, propylene and one or more non-conjugated diene(s), and the monomer components may be polymerized using Ziegler-Natta, metallocene, or other organometallic compound catalyzed reactions. Satisfactory non-conjugated dienes include 5-ethylidene-2-norbornene (referred to as ENB or EP(ENB)DM); 1,4-hexadiene (HD); 5-methylene-2-norbornene (MNB); 1,6-octadiene; 5-methyl-1,4-hexadiene; 3,7-dimethyl-1,6-octadiene; 1,3-cyclopentadiene; 1,4-cyclohexadiene; dicyclopentadiene (DCPD); 5-vinyl-2-norbornene (referred to as VNB or EP(VNB)DM); divinyl benzene, and the like, or combinations thereof. Such elastomers have the ability to produce thermoplastic vulcanizates with a cure state generally in excess of about 95 percent while maintaining physical properties attributable to the crystalline or semi-crystalline polymer. EP elastomer and EPDM elastomer with intrinsic viscosity ($\eta$) measured in Decalin at 135° C. between 0.1 to 10 dl/gram are preferred. In a particularly preferred embodiment, the elastomer is EPDM.

Suitable diene monomers may include 5-ethylidene-2-norbornene and 5-vinyl-2-norbornene. In the event that the copolymer is prepared from ethylene, alpha-olefin, and diene monomers, the copolymer may be referred to as a terpolymer or even a tetrapolymer in the event that multiple olefins or dienes are used.

The elastomeric copolymers may contain from about 20 to about 90 mole percent ethylene units derived from ethylene monomer. Preferably, these copolymers contain from about 40 to about 85 mole percent, and even more preferably from about 50 to about 80 mole percent ethylene units. Furthermore, where the copolymers contain diene units, the diene units can be present in an amount from about 0.1 to about 5 mole percent, preferably from about 0.1 to about 4 mole percent, and even more preferably from about 0.15 to about 2.5 mole percent. The balance of the copolymer will generally be made up of units derived from alpha-olefin monomers. Accordingly, the copolymer may contain from about 10 to about 80 mole percent, preferably from about 15 to about 50 mole percent, and more preferably from about 20 to about 40 mole percent alpha-olefin units derived from alpha-olefin monomers. The foregoing mole percentages are based upon the total moles of the polymer.

Suitable elastomeric copolymers for use with polyolefin thermoplastics may include the cyclic olefin copolymer elastomers known in the art. Such are particularly suitable with the high melting point cyclic olefin copolymer engineering resins.

The elastomeric copolymers may have a weight average molecular weight that is greater than about 200,000, more preferably from about 300,000 to greater than about 1,000,000, even more preferably from about 400,000 to greater than about 700,000. These copolymers preferably have a number average molecular weight that is greater than about 70,000, more preferably from about 100,000 to about 350,000, even more preferably from about 120,000 to about 300,000, and still more preferably from about 130,000 to about 250,000. Elastomers, especially those in the high end of the molecular weight range, are often oil extended in the manufacturing process and can be directly processed as such in accordance with the invention process.

Useful elastomeric copolymers preferably have a Mooney Viscosity ML [(1+4@125° C.)] of from about 10 to about 250, more preferably from about 30 to about 200, and even more preferably from about 50 to about 200, and MST [(5+4)@200° C.] below about 150, where the Mooney Viscosity is that of the non-oil extended elastomer.

Butyl elastomers may also be useful in the thermoplastic vulcanizate compositions. As used in the specification and claims, the term "butyl elastomer" includes copolymers of an isoolefin and a conjugated diolefin, terpolymers of an isoolefin with or without a conjugated diolefin, divinyl aromatic monomers and the halogenated derivatives of such copolymers and terpolymers. The halogenated versions thereof are particularly useful, especially brominated butyl elastomer. Another suitable copolymer within the scope of the olefin elastomer of the present invention is a copolymer of a C4-7 isomonoolefin and a para-alkylstyrene, and preferably a halogenated derivative thereof. The amount of halogen in the copolymer, predominantly in the para-alkylstyrene, is from 0.1 to 10% by weight. A preferred example is the brominated copolymer of isobutylene and para-methylstyrene.

The vulcanizable elastomer can also be natural elastomers or synthetic homo- or copolymers of at least one conjugated diene with an aromatic monomer, such as styrene, or a polar monomer such as acrylonitrile or alkyl-substituted acrylonitrile monomer(s) having from 3 to 8 carbon atoms. Those elastomers are higher in unsaturation than EPDM elastomer or butyl elastomer. Those elastomers can optionally be partially hydrogenated to increase thermal and oxidative stability. Desirably those elastomers have at least 50 weight percent repeat units from at least one conjugated diene monomer having from 4 to 8 carbon atoms. Other comonomers desirably include repeat units from monomers having unsaturated carboxylic acids, unsaturated dicarboxylic acids, unsaturated anhydrides of dicarboxylic acids, and include divinylbenzene, alkylacrylates and other monomers having from 3 to 20 carbon atoms.

The synthetic elastomer can be nonpolar or polar depending on the comonomers. Examples of synthetic elastomers include synthetic polyisoprene, polybutadiene elastomer, styrene-butadiene elastomer (SBR), butadiene-acrylonitrile elastomer, etc. Amine-functionalized, carboxy-functionalized or epoxy-functionalized synthetic elastomers may be used, and examples of these include maleated EPDM, and epoxy-functionalized natural elastomers. These materials are commercially available. Non-polar elastomers are preferred; polar elastomers may be used but may require the use of one or more compatibilizers, as is well known to those skilled in the art.

Suitable elastomers for use in accordance with the present invention may also include hydrogenated styrenic triblock copolymer elastomers, exemplified by SEBS (styrene/ethylene-butylene/styrene), SEPS (styrene/ethylene-propylene/styrene), SEEPS (styrene/ethylene-ethylene-propylene/styrene), which are widely available. As noted in the aforementioned reference, hydrogenated styrenic triblock copolymers may include crosslinkable styrenic blocks, which, in combination with the crosslinkable midblocks, may afford greater overall crosslinking of the cured elastomer within the TPV. These elastomers may have a styrene content as low as about 10% by weight to as high as about 50% by weight, preferably about 20% and about 40% by weight, and most preferably from about 25% to about 35% by weight. The molecular weight of the styrene component may be from about 7,000 to about 50,000 and the molecular weight of the elastomeric component may be from about 30,000 to greater than 150,000.

The thermoplastic vulcanizate composition further includes at least one thermoplastic, which in one embodiment is a polyolefin. In one embodiment, the TPV may comprise from about 80% to about 20% by weight, and in another embodiment, from about 70% to about 30% by weight, and in yet another embodiment from about 65% to about 35% by weight and in still yet another embodiment, from about 60% to about 40% by weight, of a thermoplastic, which may comprise one or more than one thermoplastic.

Suitable thermoplastics used in the invention may include crystalline or a semi-crystalline thermoplastics, and of such, more preferably is a thermoplastic that has a crystallinity of at least 10 percent as measured by differential scanning calorimetry. Polymers with a high glass transition temperature, e.g., non-crystalline glassy engineering thermoplastics, are also acceptable as the thermoplastic. Suitable thermoplastics generally are those with a melt temperature lower than the decomposition temperature of the elastomer. Thus both polar and non-polar thermoplastics can be utilized in the current invention. As used herein, reference to a thermoplastic or thermoplastic may include a mixture of two or more different thermoplastics or a blend of one or more compatibilizers and one or more thermoplastics.

Exemplary thermoplastics may include crystallizable polyolefins (such as homopolymers and copolymers of ethylene or propylene, and copolymers with cyclic olefins), polyimides, polyamides (nylons), polyesters, thermoplastic copolyesters or copolyamides, poly(phenylene ether), polycarbonates, styrene-acrylonitrile copolymers, polyethylene terephthalate, polybutylene terephthalate, polystyrene, polystyrene derivatives, polyphenylene oxide, polyoxymethylene, polymethymethacrylates, fluorine-containing thermoplastics and polyurethanes. The preferred thermoplastics are crystallizable polyolefins that are formed by polymerizing alpha-olefins such as ethylene, propylene, 1-butene, 1-hexene, 1-octene, 2-methyl-1-propene, 3-methyl-1-pentene, 4-methyl-1-pentene, 5-methyl-1-hexene, and mixtures thereof. For example, known ethylene-based homo- and copolymers having ethylene crystallinity are suitable. Commercial products include high density polyethylene (HDPE), linear low density polyethylene (LLDPE), and very low density polyethylene (VLDPE, or plastomers). Propylene-based homopolymers and copolymers, such as isotactic polypropylene and crystallizable copolymers of propylene and ethylene or other C4-C10 alpha-olefins, or diolefins, having isotactic propylene crystallinity, are preferred. Copolymers of ethylene and propylene or ethylene or propylene with another alpha-olefin such as 1-butene, 1-hexene, 1-octene, 2-methyl-1-propene, 3-methyl-1-petene, 4-methyl-1-pentene, 5-methyl-1-hexene or mixtures thereof are also suitable. These will include reactor polypropylene copolymers and impact polypropylene copolymers, whether block, random or of mixed polymer synthesis. These homopolymers and copolymers may be synthesized by using any polymerization technique known in the art such as, but not limited to, the "Phillips catalyzed reactions," conventional Ziegler-Natta type polymerizations, and organometallic, single-site olefin polymerization catalysis exemplified by, but not limited to, metallocene-alumoxane and metallocene-ionic activator catalysis.

Polyolefin thermoplastics may have a weight average molecular weight (Mw) from about 50,000 to about 600,000, and a number average molecular weight (Mn) from about 50,000 to about 200,000. These resins have a Mw from about 150,000 to about 500,000, and an Mn from about 65,000 to about 150,000. The molecular weight can typically be determined by gel permeation chromatography (GPC) using a suitable standard for the thermoplastic being measured. Additionally, Mn and polymer structure can be measured using Differential Refractive Index (DRI) detectors and Mw can be measured using Low Angle Light Scattering (LALLS). ASTM D 6474 provides a general description for polyolefins, see also ISO 11344 and T. Sun, 34 Macromolecules 6812 (2001) for adaptation for synthetic elastomer.

Additionally, cyclic olefin copolymers can be used as high melting point polyolefin thermoplastics. Preferred cyclic olefins include cyclobutene, cyclopentene, cyclooctene, norbornene, 5-methyl-norbornene, 3-methyl-norbornene, ethyl-norbornene, phenyl-norbornene, dimethyl-norbornene, diethyl-norbornene, dicyclopentadiene, tetracyclododecene, methyltetracyclododecene, and the like. Lower carbon number alpha-olefins, e.g., C3-C8, can be used as comonomers, for disruption of crystallinity and reduction of melting point. Ethylene is a particularly preferred comonomer in the cyclic olefin copolymers.

The crystalline or semi-crystalline thermoplastics generally have a melt temperature (Tm) that is from about 40° C. to about 350° C., preferably from about 60° C. to about 210° C., more preferably from about 90° C. to about 180° C., and even more preferably from about 120° C. to about 170° C. The glass transition temperature (Tg) of these thermoplastics is from about −25° C. to about 10° C., preferably from about −5 to about 5° C. More generally speaking, including the semi-crystalline and glassy polar thermoplastics, useful thermoplastics will have a Tg of up to and greater than 100° C., and even greater than 150° C. The characterizing temperatures are determined by DSC according to the test method of ASTM D-3418.

One commercially available thermoplastic is highly crystalline isotactic or syndiotactic polypropylene. This polypropylene generally has a density of from about 0.85 to about 0.91 g/cc, with the largely isotactic polypropylene having a density of from about 0.90 to about 0.91 g/cc. Also, high and ultra-high molecular weight polypropylene that has a fractional melt flow rate is highly preferred. These polypropylene resins are characterized by a melt flow rate that is from 0.2 to 3000 dg/min and more preferably less than 1.2 dg/min, and most preferably less than or equal to 0.8 dg/min per ASTM D-1238. Melt flow rate is a measure of how easily a polymer flows under standard pressure, and is measured by using ASTM D-1238 at 230° C. and 2.16 kg load.

The TPV composition further comprises an amount of a methacrylate monomer coagent, which is suitable for use as a coagent in conjunction with a peroxide curing process which may be selected for curing the elastomer in the thermoplastic vulcanizate composition. The term "multifunctional methacrylate coagent" refers to monomers or low molecular weight polymers having two or more functional groups with a high response to free radicals, wherein at least two of the functional groups are a methacrylate. In the preferred embodiment, the multifunctional methacrylate monomer is trimetholpropane trimethacrylate ("TMPTMA") however, other multifunctional methacrylate monomers known in the art may include ethyleneglycol dimethacrylate, diethyleneglycol dimethacrylate, polyethyleneglycol dimethacrylate, tetraethyleneglycol dimethacrylate, hexanediol 1,6-dimethacrylate, 1,2-butyleneglycol dimethacrylate, ethoxylated and metallic derivative like zinc dimethacrylate. The coagent is suitably present in an amount between about 0.05 phr to about 12 phr. In other embodiments, the coagent may be present in an amount from about 1 phr to about 10 phr, in still other embodiments from about 1.5 phr to about 9 phr, and in still further embodiments from about 2 phr to about 8.5 phr, wherein a desirable range of multifunctional methacrylate coagent includes any combination of any upper limit with any lower limit described herein.

In conjunction with the coagent, it is noted above that the elastomer of the TPV composition is cured by means of a peroxide curing agent. The peroxide curing agent is preferably an organic peroxide. Suitable organic peroxides may have a half life of at least one hour at 120° C. Illustrative peroxides include a series of vulcanizing and polymerization agents that contain α, α'-bis(t-butylperoxy)-diisopropylbenzene and are available from Hercules, Inc. under the trade designation VULCUP™, a series of such agents that contain dicumyl peroxide and are available from Hercules, Inc. under the trade designation Di-cup™, as well as Lupersol™, peroxides made by Elf Atochem, North America, or Trigonox™, Organic peroxides made by Akzo Nobel. The Lupersol™ peroxides include Lupersol™ 101 (2,5-dimethyl-2,5-di(t-butylperoxy)hexane), Lupersol™ 130 (2,5-dimethyl-2,5-di(t-butylperoxy)hexyne-3) and Lupersol™ 575 (t-amyl peroxy)-2-ethylhexonate). Other suitable peroxides include 2,5-dimethyl-2,5-di-(t-butyl peroxy)hexane, di-t-butylperoxide, di-(t-amyl)peroxide, 2,5-di(t-amyl peroxy)-2,5-dimethylhexane, 2,5-di-(t-butylperoxy)-2,5-diphenylhexane, bis(alpha-methylbenzyl)peroxide, benzoylperoxide, t-butylperbenzoate, 3,6,9-triethyl-3,6,9-trimethyl-1,4,7-triperoxonane and bis(t-butylperoxy)-diisopropylbenzene. The peroxide is suitably present in the TPV composition in an amount of between about 0.05 to about 10 phr and in another embodiment from about 0.5 to about 8 phr and in still yet another embodiment from about 1 to about 6.5 phr. In still other embodiments, the amount may be from about 4 phr to about 7 phr. It will be understood that the amount of peroxide curing agent may be selected based on the desired level of vulcanization.

In one embodiment, the elastomer component of the TPV is advantageously completely or fully cured. In yet another embodiment it is partially cured. The degree of cure can be measured by determining the amount of elastomer that is extractable from the thermoplastic vulcanizate by using cyclohexane or boiling xylene as an extractant. This method is disclosed in U.S. Pat. No. 4,311,628, which is incorporated herein by reference for purpose of U.S. patent practice. In one embodiment, the elastomer has a degree of cure where not more than 10 weight percent, in other embodiments not more than 6 weight percent, in other embodiments not more than 5 weight percent, and in other embodiments not more than 3 weight percent is extractable by cyclohexane at 23° C. as described in U.S. Pat. No. 5,100,947 and U.S. Pat. No. 5,157,081. For purposes herein, the elastomer is "partially cured" 6 weight percent or more is extractable. Alternatively, in one or more embodiments, the elastomer has a degree of cure (dynamically-cured in a preferred embodiment) such that the crosslink density is preferably at least $4 \times 10^{-5}$, in other embodiments at least $7 \times 10^{-5}$, and in other embodiments at least $10 \times 10^{-5}$ moles per milliliter of rubber. See also "Crosslink Densities and Phase Morphologies in Dynamically Vulcanized TPEs," by Ellul et al., 68 RUBBER CHEMISTRY AND TECHNOLOGY 573-584 (1995).

In one embodiment the TPV composition also comprises at least one phosphorous containing stabilizer, which in one embodiment is an organic phosphite or organic phosphonite stabilizer. Stated another way, at least one phosphorous containing stabilizer is present during vulcanization of the elastomer/thermoplastic composition. The organic phosphate compounds can be represented by the formula $P(OR)_3$, wherein each R group is independently selected from C1 to C15 alkyl groups, C6 to C20 aryl groups, C7 to C28 arylalkyl groups, C7 to C28 alkylaryl groups, and substituted versions thereof. Examples of "substituents" include halogens, hydroxyl, nitrate and carboxylate groups. In one embodiment, one or more "R" groups are bound together through a covalent or other chemical bond. The organic phosphonite stabilizer can be represented by the formula $R_n P(OR)_{3-n}$, wherein each "R" group is as defined above; and in one embodiment, one or more "R" groups are bound together through a covalent or other chemical bond.

Exemplary stabilizers include, but are not limited to, tris (2,4-di-t-butylphenyl) phosphite available from Ciba-Geigy as Irganox 168; 2,4,6-di-t-butylphenyl-2-butyl-2-ethyl-1,3-propanediol phosphite available from General Electric, as Ultranox 641; bis(2,4-di-t-butylphenyl)pentaerythritol diphosphite available from General Electric, as Ultranox 626;

tetrakis(2,4-di-tert-butylphenyl)-4,4'-biphenylylenediphosphonite available from Ciba-Geigy, as Irgafos P-EPQ; tris[2-tert-butyl-4-thio(2'-methyl-4'-hydroxy-5-tertbutyl)phenyl-5-methyl] phenylphosphite available from Clariant, as Hostanox; 2,2',2''-nitrilotriethyl-tris [3,3',5,5'-tetra-tert-butyl-1,1'-biphenyl-2,2'-diyl] phosphite available from Ciba-Geigy, as Irgafos 1,2-distearylpentaerylthritol diphosphite, and tris(nonylphenyl) phosphite. The phosphorous containing stabilizer may be present in the thermoplastic vulcanizate composition, or stated another way, present in the elastomer/thermoplastic composition during cure, in amounts from about 0.02 to about 8 parts phr and in another embodiment from about 0.2 to about 6 phr and in still yet another embodiment from about 1 to about 5 phr, wherein a desirable range includes any upper limit disclosed herein combined with any lower limit described herein.

Common additives, which may be incorporated in selected amounts in the TPV compositions may include, among others known in the art, reinforcing and non-reinforcing fillers, fibers (like glass, carbon fibers or carbon fibrils), processing oils, extender oils, thermoplasticizers, waxes, UV and heat, antioxidants, processing aids, lubricants, foaming agents, flame retardant packages, pigments and other coloring agents. Fillers and extenders which can be utilized include conventional inorganic substances, such as calcium carbonate, clays, silica, talc, nano composites; such as nano clay, titanium dioxide, carbon black and the like. Some materials, such as some fillers, can serve a plurality of functions. For instance, antimony trioxide can function as a filler and also provide, preferably in combination with other materials, some flame retardancy to the present thermoplastic vulcanizate composition. Suitable flame retardant include halogenated organic derivative like brominated derivative or non-halogenated derivative like $Al(OH)_3$ or $Mg(OH)_2$ or polyphosphate or polyphosphonites. Suitable smoke suppressors include Zinc Borate. In general, suitable elastomer processing oils are paraffinic, naphthenic or aromatic oils derived from petroleum fractions or synthetic process oil like SpectraSyn from ExxonMobil. The viscosity of the process oil can be from about 5 cSt to about 1000 cSt measured at 100° C. The amount of total process oil (including oil coming from oil extended elastomer if such elastomer is used) can be from 0 to 300 phr, preferably from 50 to 200 phr. The type of the oil selected can be one that ordinarily is used in combination with the specific elastomer or elastomers in the present composition. These additives can comprise a significant amount of the total formulated composition. More particularly, when present, one or more additives can be present in amounts greater than 0 parts per hundred elastomer to approximately 500 phr including total process oil, and more generally up to about 300 phr.

In order to improve the long term heat stability and UV resistance of the exemplary TPV compositions of the present application, the TPV compositions may contain an amount of heat stabilizer which may be one or several of any type of phenolic or thioether or thiobisphenols. Optionally aromatic amine based heat stabilizers, which are also known in the art may be used. Still further, aminophenols may be used. Where present, the amount of heat stabilizers may be from about 0.01 to about 6 phr.

UV resistance may be improved by addition of an amount of UV stabilizer; preferably from about 0.1 to about 6 phr. Suitable UV stabilizers may include any type of hindered amine light stabilizer, (referred to as "HALS"). HALS are derivatives of 2,2,6,6-tetramethyl piperidine. Examples of suitable hindered amines may include bis(2,2,6,6-tetramethyl-4-piperidinyl)sebacate, bis(1,2,2,6,6-pentamethyl-4-piperidinyl)sebacate, bis(1,2,2,6,6-pentamethyl-4-piperidinyl)2-n-butyl-(3,5-di-tert-butyl-hydroxy-benzyl)malonate, 8-acetyl-3-dodecyl-7,7,9,9-tetramethly-1,3,8-triazaspirol(4,5)decane-2,4-dione, tetra(2,2,6,6-tetramethyl-4-piperidinyl) 1,2,3,4-butanetetracarboxylate, 1-(-2-[3,5-di-tert-butyl-4-hydroxyphenyl-propionyloxyl]ethyl)-4-(3,5-di-tert-butyl-4-hydroxyphenylpropionyloxy)-2,2,6,6-tetramethylpiperidine, 1,1'-(1,2-ethenadiyl)bis(3,3,5,5-tetramethyl-2-piperazinone), 1,3,5-triazine-2,4,6-triamine, N,N'''-[1,2-ethanediylbis[[[4,6-bis(butyl(1,2,2,6,6-pentamethyl-4-piperidinyl)amino]-1,3,5-triazine-2-yl] imino]-3,1-propanediyl]]-bis[N',N'''-dibutyl-N',N'''-bis(1,2,2,6,6-pentamethyl-4-piperidinyl), 7-oxa-3,20-diazadispiro [5.1.11.2]heneicosan-21-one-2,2,4,4-tetramethyl-20-oxiranylmethyl), homopolymer (9CI), and blends thereof.

In conjunction with or in addition to the amount of UV stabilizer, the exemplary compositions may contain one or more UV absorber of the benzophenone or benzo triazole variety. Suitable UV absorbers may include one or a blend of more than one of, Octyl-p-methoxycinnamate, 2,2',4,4'-tetrahydroxy benzophenone (benzophenone 2), 2,2'-dihydroxy-4,4'-dimethoxy benzophenone (benzophenone 6), 2,2'-dihydroxy-4,4'-dimethoxy benzophenone-5,5'-disodium sulfonate (benzophenone 9), 2,3,4,4'-tetrahydroxy benzophenone, 2,3,4-trihydroxy benzophenone, 2,4-dihydroxy benzophenone (bp-1), 2-hydroxy-4-methoxy benzophenone (benzophenone 3), 2-hydroxy-4-methoxy benzophenone-5-sulfonic acid (benzophenone 4), 2-hydroxy-4-methoxy benzophenone-5-sodium sulfonate (benzophenone 5), 2,2'-dihydroxy-4-methoxy benzophenone (benzophenone 8), 2-hydroxy-4-octyloxy benzophenone (benzophenone 12), 4-chloro-4'-hydroxybenzophenone, 2-hydroxy-4-laurylbenzophenone, 4,4'-dlhydroxybenzophenone, 2-hydroxy-4-lanrylbenzophenone, 2,2'3,4,4'-pentahydroxy benzophenone, 2,3,3',4,4',5'-hexahydroxy benzophenone, 2,4,6,3',4'-pentahydroxy-benzophenone, 4,4'-diamionbenzophenone (dabp), 4,4'-dichlorobenzophenone (dcbp), 3,3',4,4'-benzophenone tetracarboxylic acid, 3,3',4,4'-diphenylketonetetracarboxylic acid, 3,4-dihydroxybenzophenone, 2,2',4-trihydroxybenzophenone, 2,4-dimethoxy-2'-hydroxybenzophenone, 3,4-dihydroxy-5-methoxybenzaldehyde, 2-hydroxy-benzophenone, 4-hydroxy-benzophenone, 2,2,4'-trihydroxybenzophenone, 4-tert-butyl-4'-methoxy-dibenzolmethane, Parsol-1789 octyl salicylate, 2-ethylhexyl 2-cyano-3,3-diphenyl-acrylate, octocrylene, p-methoxycinnamic acid 2-ethylhexyl ester, 2-(2'-hydroxy-5'-methylphenyl)benzotriazole, 2-(2'-hydroxy-3',5'-di-tert-butylphenyl)-5-chlorobenzotriazole, 2-(3'-tert-butyl-2-hydroxy-5'-methylphenyl)-5-chlorabenzotriazole, 2-(2'-hydroxyl-5'-t-octylphenyl)benzotriazole, 2-(2'-hydroxy-3',5'-ditertamyl phenyl) benzotriazole, Phenylbenzimidazole sulfonic acid, Ensulizole, Uv-1200, Tinuvin™ 1130, 2-(2h-benzotriazol-2-yl)-6-dodecyl-4-methylphenol, 2-[2'-hydroxy-3',5'-bis(-dimethylbenzyl)-phenyl] benzotriazole, 2-(2h-benzotriazol-2-yl)-4,6-bis(1,1-dimethylethyl)-phenol, bis(2,2,6,6-tetramethyl-4-piperidine)sebacate, and methylene bis[(3-(2-benzotriazolyl)-2-hydroxy-5-tert-octylphenyl].

According to the present invention, TPVs having superior extrusion performance may be formed by melt blending, in a chamber, a composition comprising the elastomer, thermoplastic, peroxide curing agent, multifunctional methacrylate monomer coagent and phosphorous containing stabilizer in the amounts described above. The chamber may be any vessel that is suitable for blending the selected composition under temperature and shearing force conditions necessary to form a thermoplastic vulcanizate. In this respect, the chamber may be a mixer, such as a Banbury™ mixer, or a mill, or an extruder. According to one embodiment, the chamber is an extruder, which may be a single or multi-screw extruder. The term "multi-screw extruder" means an extruder having two or more screws; with two and three screw extruders being exemplary, and two or twin screw extruders being preferred. The screws of the extruder may have a plurality of lobes; two and three lobe screws being preferred. It will be readily understood that other screw designs may be selected in accordance with the methods of the present invention.

The blending is generally performed at a temperature not exceeding 400° C., preferably not exceeding 300° C. and more particularly not exceeding 250° C. The minimum temperature at which the melt blending is performed is generally higher than or equal to 130° C., preferably higher than or equal to 150° C. and more particularly higher than 180° C. The blending time is chosen by taking into account the nature of the compounds used in the TPV composition and the blending temperature. The time generally varies from 5 second to 120 minutes, and in most cases from 10 seconds to about 30 minutes. The TPVs prepared in conjunction with this invention were prepared in a twin screw extruder equipped with co-rotating screws and 12 barrels. Two vent ports were utilized in barrel sections #6 and #11 for devolatalization of any decomposed peroxide residual and volatiles including moisture.

It is noted that one benefit of the exemplary TPV compositions is reduced die lip buildup on extrusion of the thermoplastic vulcanizate. In one embodiment, the melt blend of the peroxide cured TPV having the multifunctional methacrylate coagent and at least one phosphorus containing stabilizer is extruded from an extruder, and the resulting extrudate does not show die-lip buildup at 5 minutes. For purposes of the present invention, die lip buildup was characterized in accordance with the following exemplary testing method:

The thermoplastic vulcanizate formed according to the compositions and methods described above (and in the Examples below) were tested in a 1.25 inch Diamond America™ single screw extruder. The extruder was equipped with a grooved barrel, a two stage screw, and 20-40-20-40 melt screen pack. A Bauknecht™ extrusion profile die was used for the study. The TPV material was not dried for the tests. The extruder was purged for approximately 5 minute and then the die was cleaned. The extruder rpm was set at 100 and the extruder output was approximately 11 kg/hr. The temperature profile of the extruder was 185, 190, 200, 205, and 205 (die) ° C. In one embodiment, the resulting melt-blended thermoplastic vulcanizate extrudate does not show die-lip buildup after 5 minutes when extruded in a grooved barrel, single screw extruder using a Bauknecht™ extrusion profile die set at 205° C. at an output of 11 kg/hr, the other elements of the extruder at a set point of between 180 and 208° C.

Upon die cleaning of extrusion the die lip was monitored and two points were quantitatively measured. The first measurement was the time until visible die lip buildup. This refers to the first visible appearance of build up at the die lip. The second measurement was the time until die lip buildup was sufficient to start dripping, that is, by force of gravity, chunks of extrudate material would drop from the edge of the die from where it was building up into a mass. Thus, in relation to the examples described below, time to visible die lip buildup and time to moustache drip are disclosed. An indication of the severity of die moustache at 15 minutes post extrusion commencement is also recorded. As demonstrated in the examples below, the exemplary TPV compositions having the multifunctional methacrylate monomer coagent and the phosphorous containing stabilizer of the present invention showed significant improvement in the time to visible die lip buildup over conventionally prepared TPVs using other stabilizers and peroxide curing coagents. To further elucidate the improvement the following examples are offered.

EXAMPLE 1

Example 1 demonstrates the reduction of die lip build up in thermoplastic vulcanizates prepared with a multifuinctional methacrylate monomer coagent and a phosphorus containing stabilizer. In the following examples, Flowsperse FPC (SR350)50 from Flowpolymers, 50% of SR350 from Sartomer in synthetic filler was used as the multifunctional methacrylate monomer coatent. In the Comparative examples, other conventional peroxide cure coagents, namely Ricon 154D polybutadiene resin (from Sartomer) and PLC(TAC) 50BC triallyl cyanurate (from Rhein-Chemie, 50% TAC in clay), Flowsperse PLC604, multifunctional acrylate monomer coagent (from Flowpolymers, 75% TMPTA in 25% synthetic calcium silicate) were used. Example 1 also demonstrates that within TPVs formed with the multifunctional methacrylate monomer coagent, TPVs formed in the presence of a commercially available stabilizer package that includes a phosphite stabilizer (Ultranox 626) showed improved die lip buildup as compared to TPVs prepared with stabilizer packages that did not include phosphite stabilizers.

In Example 1, all sample and comparative TPVs were formed from a blend in-cluding 200 phr of EPDM elastomer (EP(VNB) ethylene 63%, 0.7% VNB, by weight, extended with 100 phr Sunpar 150 LW paraffinic oil, Mooney Viscosity ML(1+4) at 125° C.=52 and inherent viscosity in Decalin at 135° C.=4.7), a total of 59 phr of isotactic polypropylene (Sunoco F008F(™)), and a total of 42 phr of clay (39 phr+3 phr with stabilizer mixture, Icecap K clay from Burgess Pigments). Each composition was cured with 6.5 phr of organic peroxide (DHBP-50-WO™ available from Degussa, 2,5-Dimethyl-2,5-di(t-butylperoxy)hexane diluted in 50% white mineral oil) to vulcanize the elastomer. Additional amounts of processing oil (Sunpar 2280 from Sun Oil, paraffinic oil) and zinc oxide (Kodax 911 from Zinc Co.) were added to aid in processing the TPV as shown in Table 1. As indicated in Table 1, for purposes of this Example, as well as Examples 2 and 3 (discussed below) the thermoplastic was injected into the extruder in two portions. In Example 1, thermoplastic portion 1 (35 phr) was introduced at barrel 1. Portion 2 (24 phr) was introduced at barrel 9.

As indicated in Table 1, Sample TPV composition 1 further included 8.1 phr of the multifunctional methacrylate monomer coagent TMPTMA (Flowsperse FPC(SR 350) 50 and 4.14 phr of Stabilizer Package #3, which comprises a phenolic antioxidant stabilizer (Irganox 1035) (1.38 phr), phosphite stabilizer (Ultranox 626) (1.38 phr) and synthetic hydrotalcite (DHT-4A) (1.38 phr) as acid scavenger from Kyowa Chemical Industry Co., Ltd. See Table 2 for the compositions of the respective Stabilizer Packages referred to in each of the Examples.

In contrast, Comparative TPV composition 1 included 8.1 phr of the TMPTMA and 4.12 phr of Stabilizer Package #1, which comprises high molecular weight hydroxylamine stabilizer (Irgastab FS 210FF) (1.38 phr), thioether stabilizer (Irganox PS802) (0.68 phr), antioxidant synergist (Vanox ZMTI) (0.68 phr), and synthetic hydrotalcite stabilizer (DHT-4A) (1.38 phr).

Comparative TPV composition 2 was formed with 3 phr of peroxide curing coagent triallyl cyanurate PLC (TAC) 50 BC in place of the TMPTMA of the Sample TPV composition 1 and 4.14 phr of Stabilizer Package 3.

Comparative TPV preparation 3 was formed with 3 phr of PLC (TAC) 50 BC and 4.14 parts of Stabilizer Package 2, which comprises aralkyl-substituted diphenyl amine (Naugard 445) (0.68 phr), (Irgastab FS 210FF) (1.38 phr), (Irganox 1035) (0.68 phr), and (DHT-4A) (1.38 phr).

Comparative TPV composition 4 comprised 10 phr of Ricon 154 D and 4.12 phr of Stabilizer Package 1.

Comparative TPV composition 5 was formed with 5 phr of Ricon 154 D and 4.05 phr of TMPTMA and 4.12 phr of Stabilizer Package 1.

Comparative TPV composition 6 was formed with 4.8 phr of Flowsperse PLC-604 and 4.12 phr of Stabilizer Package 1.

Table 1 details the compositions of each of the sample and comparative ("Comp") TPVs discussed in this example. Table 3 provides data on the mechanical and physical properties on the Sample and Comparative TPVs. Table 4 provides data on time to visible die moustache buildup and time to moustache drip as tested according to the method described above. Additionally, an indication of the severity of die moustache at 15 minutes post extrusion commencement is provided.

TPV Compositions (Example 1)

Mechanical and physical properties (Table 3) for all examples were evaluated as follows:
1. Shore Hardness according to ASTM D-2240.
2. Ultimate tensile strength and elongation and tensile modulus at 100% elongation according to ASTM D-412.
3. Weight gain according to ASTM D-471 after 24 hours at 125° C.
4. Tension set at room temperature according to ASTM D-412 (100% stretching, 10 minutes stretching time, 10 minutes relaxation time).
5. Compression set at 25% compression according to ASTM D-395.
6. Color parameters (L, a, b) values are measured by a Labscan XE Color Spectrophotometer from Hunter Labs.
7. Shear Viscosity (LCR) is measured by a capillary rheometer LSR 6000 Model 6052 M-513 supplied by Dynisco between shear rate of 100 to 10000 second$^{-1}$ and viscosity at 1200 second$^{-1}$ obtained by interpolation is reported in Pa.s.

TABLE 1

| (phr) | Inj. Loc. BS# | TPV #1 | Comp. TPV #1 | Comp. TPV #2 | Comp. TPV #3 | Comp. TPV #4 | Comp. TPV #5 | Comp. TPV #6 |
|---|---|---|---|---|---|---|---|---|
| Elastomer | 1 | 200 | 200 | 200 | 200 | 200 | 200 | 200 |
| Plastic | 1 | 35 | 35 | 35 | 35 | 35 | 35 | 35 |
| Plastic | 9 | 24 | 24 | 24 | 24 | 24 | 24 | 24 |
| Peroxide | 3 | 6.5 | 6.5 | 6.5 | 6.5 | 6.5 | 6.5 | 6.5 |
| Clay | 1 | 39 | 39 | 39 | 39 | 39 | 39 | 39 |
| ZnO | 1 | 1.94 | 1.94 | 1.94 | 1.94 | 1.94 | 1.94 | 1.94 |
| Processing Oil | 2 | 14 | 14 | 14 | 14 | 14 | 14 | 14 |
| Processing Oil | 8 | 17.65 | 17.65 | 17.65 | 17.65 | 17.65 | 17.65 | 17.65 |
| Flowsperse FPC(SR350)50 | 1 | 8.1 | 8.1 | — | — | — | — | — |
| PLC(TAC)50BC | 1 | — | — | 3 | 3 | — | — | — |
| Ricon154D | 1 | — | — | — | — | 10 | — | — |
| Ricon154D/ Flowsperse FPC(SR350)50 | 1 | — | — | — | — | — | 5/4.05 | — |
| Flowsperse PLC-604 | 1 | — | — | — | — | — | — | 4.80 |
| Stabilizer package #1 | 1 | — | 4.12 | — | — | 4.12 | 4.12 | 4.12 |
| Stabilizer package #2 | 1 | — | — | — | 4.14 | — | — | — |
| Stabilizer package #3 | 1 | 4.14 | — | 4.14 | — | — | — | — |

TABLE 2

Composition of Stabilizer Packages

| Stabilizers | Package #1 (in phr) | Package #2 (in phr) | Package #3 (in phr) |
|---|---|---|---|
| Irgastab FS210FF | 1.38 | 1.38 | — |
| Irganox PS802 | 0.68 | — | — |
| Vanox ZMTI | 0.68 | — | — |
| DHT-4A | 1.38 | 1.38 | 1.38 |
| Naugard 445 | — | 0.68 | — |
| Irganox 1035 | — | 0.68 | 1.38 |
| Ultranox 626 | — | — | 1.38 |

TABLE 3

Physical Property Data

| | TPV #1 | Comp TPV #1 | Comp TPV #2 | Comp TPV #3 | Comp TPV #4 | Comp TPV #5 | Comp TPV #6 |
|---|---|---|---|---|---|---|---|
| Hardness (Shore A) | 69.3 | 67.4 | 64.0 | 64.4 | 66.7 | 69.2 | 62.9 |
| UTS (psi) | 1069 | 1076 | 991 | 1006 | 1002 | 959 | 830 |
| UE (%) | 509 | 503 | 523 | 532 | 443 | 463 | 453 |

TABLE 3-continued

Physical Property Data

|  | TPV #1 | Comp TPV #1 | Comp TPV #2 | Comp TPV #3 | Comp TPV #4 | Comp TPV #5 | Comp TPV #6 |
|---|---|---|---|---|---|---|---|
| M100 (psi) | 370 | 357 | 322 | 316 | 354 | 382 | 302 |
| Weight Gain (%) | 103 | 95.3 | 99.8 | 109.4 | 98.9 | 95.6 | 122.3 |
| L | 84.15 | 83.85 | 82.68 | 83.61 | 78.61 | 80.72 | 81.17 |
| a | −1.42 | −1.24 | −1.57 | −1.55 | −0.61 | −0.95 | −1.41 |
| b | 5.83 | 6.47 | 6.27 | 7.48 | 5.61 | 6.02 | 6.15 |
| LCR (Pa · s) | 75 | 68 | 67 | 67 | 65 | 65 | 56 |
| Tension Set (%) | 11.5 | 14.0 | 14 | 14 | 15.0 | 15.0 | 12.5 |
| Compression Set at 100° C., 168 hr, (%) | 39 | 34 | 42 | 45 | 39 | 41 | 42 |

As demonstrated in Table 4, the Sample.TPV, which includes the TMPTMA and a stabilizer package comprising a phosphite stabilizer showed the least die moustache buildup and the least severity of die moustache buildup after 15 mins.

TABLE 4

Die Lip Buildup Data

|  | TPV #1 | Comp TPV #1 | Comp TPV #2 | Comp TPV #3 | Comp TPV #4 | Comp TPV #5 | Comp TPV #6 |
|---|---|---|---|---|---|---|---|
| Time (min), visible die mustache buildup | Started at ca.15 | <1 | <1 | <1 | <1 | <1 | <1 |
| Time (min), mustache start dripping | None at 15 | <5 | <5 | <5 | <5 | <5 | <5 |
| Severity of Die Mustache at 15 min | Very little | Little | Heavy | Heavy | Medium | Heavy | Heavy |

EXAMPLE 2

In Example 2, the Sample and Comparative TPVs of Example 1 were reformed according to the respective compositions in Table 1; however, using only 52.4 phr of thermoplastic (disposed in two portions of 31 phr and 21.4 phr respectively) so as to provide a softer TPV formulation. Table 5 lists the compositions of Sample TPV #2 and Comparative TPVs #7-#12. Table 6 provides the physical properties of the Sample and Comparative TPVs of the Example and Table 7 provides the die lip moustache buildup data. Example 2 demonstrates again the improvement seen in TPV compositions comprising both TMPTMA and a stabilizer package comprising a phosphite stabilizer.

TABLE 5

TPV Compositions (Example 2)

| (phr) | Inj. Loc. | TPV #2 | Comp TPV #7 | Comp TPV #8 | Comp TPV #9 | Comp TPV #10 | Comp TPV #11 | Comp TPV #12 |
|---|---|---|---|---|---|---|---|---|
| Elastomer | 1 | 200 | 200 | 200 | 200 | 200 | 200 | 200 |
| Plastic | 1 | 31 | 31 | 31 | 31 | 31 | 31 | 31 |
| Plastic | 9 | 21.4 | 21.4 | 21.4 | 21.4 | 21.4 | 21.4 | 21.4 |
| Peroxide | 3 | 6.5 | 6.5 | 6.5 | 6.5 | 6.5 | 6.5 | 6.5 |
| Clay | 1 | 39 | 39 | 39 | 39 | 39 | 39 | 39 |
| ZnO | 1 | 1.94 | 1.94 | 1.94 | 1.94 | 1.94 | 1.94 | 1.94 |
| Processing Oil | 2 | 14 | 14 | 14 | 14 | 14 | 14 | 14 |
| Processing Oil | 8 | 17.65 | 17.65 | 17.65 | 17.65 | 17.65 | 17.65 | 17.65 |
| Flowsperse FPC(SR350)50 | 1 | 8.1 | 8.1 | — | — | — | — | — |
| PLC(TAC)50BC | 1 | — | — | 3 | 3 | — | — | — |
| Ricon154D | 1 | — | — | — | — | 10 | — | — |
| Ricon154D/ Flowsperse FPC(SR350)50 | 1 | — | — | — | — | — | 5/4.05 | — |
| Flowsperse PLC-604 | 1 | — | — | — | — | — | — | 4.80 |
| Stabilizer package #1 | 1 | — | 4.12 | — | — | 4.12 | 4.12 | 4.12 |
| Stabilizer package #2 | 1 | — | — | — | 4.14 | — | — | — |
| Stabilizer package #3 | 1 | 4.14 | — | 4.14 | — | — | — | — |

TABLE 6

Physical Property Data

|  | TPV #2 | Comp TPV #7 | Comp TPV #8 | Comp TPV #9 | Comp TPV #10 | Comp TPV #11 | Comp TPV #12 |
|---|---|---|---|---|---|---|---|
| Hardness (Shore A) | 66.3 | 63.9 | 61.1 | 60.1 | 63.9 | 65.6 | 59.0 |
| UTS (psi) | 978 | 972 | 906 | 943 | 943 | 972 | 739 |
| UE (%) | 451 | 469 | 509 | 535 | 410 | 442 | 424 |
| M100 (psi) | 349 | 318 | 293 | 273 | 326 | 356 | 267 |
| Weight Gain (%) | 103.1 | 103.0 | 118.7 | 135 | 99.9 | 94.3 | 127.7 |
| L | 84.08 | 84.14 | 83.32 | 83 | 78.94 | 81.34 | 81.65 |
| A | −1.56 | −1.20 | −1.54 | −1.61 | −0.58 | −0.79 | −1.35 |
| B | 5.79 | 6.61 | 5.75 | 7.44 | 5.66 | 6.06 | 6.20 |
| LCR (Pa · s) | 74.7 | 68.6 | 68.7 | 70.6 | 66.5 | 66 | 57.5 |
| Tension Set (%) | 10.0 | 12.5 | 15.0 | 15.0 | 12.5 | 15.0 | 20 |
| Compression Set at 100° C., 168 hr, (%) | 36 | 36 | 41 | 41 | 36 | 35 | 40 |

TABLE 7

Die Lip Buildup Data

|  | TPV #2 | Comp TPV #7 | Comp TPV #8 | Comp TPV #9 | Comp TPV #10 | Comp TPV #11 | Comp TPV #12 |
|---|---|---|---|---|---|---|---|
| Time (min), visible die mustache buildup starts | 10 | <1 | <1 | <1 | <1 | <1 | <1 |
| Time (min), mustache start dripping | 15 | <5 | <5 | <5 | <5 | <5 | <5 |
| Severity of Die Mustache at 15 min | Little | Medium | Heavy | Heavy | Heavy | Heavy | Heavy |

EXAMPLE 3

In order to determine which of the thermoplastic stabilizers of the stabilizer package identified in Examples 1 and 2 as providing the most improved die lip buildup; namely, Stabilizer Package 3, sample TPVs 3-12 were prepared with each of the stabilizers in the package separately and in various combinations so as to enable conclusions concerning the distinction in effect on die lip buildup of specific stabilizer in the preferred stabilizer package on die lip buildup. Again, each of the TPVs was formed with 200 phr of EPDM elastomer, 59 phr of isotactic polypropylene (disposed in two portions of 35 phr and 24 phr respectively), 6.5 phr of an organic peroxide curing agent and suitable amounts of processing oils and clay. Table 8 provides the formula of each of the TPV compositions in the present example. Table 9 demonstrates the physical properties of each of the respective TPVs and Table 10 demonstrates the die moustache buildup data recorded with respect to each of the TPVs.

It is noted that the best die lip buildup property was found in relation to TPVs comprising the phosphite stabilizer Ultranox 626 as compared to TPVs comprising the phenolic stabilizer Irganox 1035. It is thus demonstrated that the combination of the TMPTMA and phosphite stabilizer affords the greatest improvement in die lip buildup. It is further demonstrated that these exemplary compositions have comparable physical properties to the other TPVs. It is thus demonstrated that die lip buildup may be selectively improved by the addition of a multifunctional methacrylate monomer coagent and a phosphite stabilizer to the TPV composition.

TABLE 8

TPV Compositions

| (phr) | Inj. Loc. | Comp TPV #13 | Comp TPV #14 | Comp TPV #15 | TPV #3 | TPV #4 | TPV #5 | TPV #6 | TPV #7 | TPV #8 | TPV #12 |
|---|---|---|---|---|---|---|---|---|---|---|---|
| Elastomer | 1 | 200 | 200 | 200 | 200 | 200 | 200 | 200 | 200 | 200 | 200 |
| Plastic | 1 | 35 | 35 | 35 | 35 | 35 | 35 | 35 | 35 | 35 | 35 |
| Plastic | 9 | 24 | 24 | 24 | 24 | 24 | 24 | 24 | 24 | 24 | 24 |
| Peroxide | 3 | 6.5 | 6.5 | 6.5 | 6.5 | 6.5 | 6.5 | 6.5 | 6.5 | 6.5 | 6.5 |
| Clay | 1 | 39 | 39 | 39 | 39 | 39 | 39 | 39 | 39 | 39 | 39 |
| ZnO |  | 1.94 | 1.94 | 1.94 | 1.94 | 1.94 | 1.94 | 1.94 | 1.94 | 1.94 | 1.94 |
| Processing Oil | 2 | 14 | 14 | 14 | 14 | 14 | 14 | 14 | 14 | 14 | 14 |
| Processing Oil | 8 | 17.65 | 17.65 | 17.65 | 17.65 | 17.65 | 17.65 | 17.65 | 17.65 | 17.65 | 17.65 |
| Flowsperse FPC (SR350)50 |  | 8.1 | 8.1 | 8.1 | 8.1 | 8.1 | 8.1 | 8.1 | 8.1 | 8.1 | 8.1 |

TABLE 8-continued

TPV Compositions

| (phr) | Inj. Loc. | Comp TPV #13 | Comp TPV #14 | Comp TPV #15 | TPV #3 | TPV #4 | TPV #5 | TPV #6 | TPV #7 | TPV #8 | TPV #12 |
|---|---|---|---|---|---|---|---|---|---|---|---|
| Irganox 1035 | | 0.68 | 1.38 | 2.76 | — | — | — | 0.68 | 1.38 | 2.76 | 1.38 |
| Ultranox 626 | | — | — | — | 0.76 | 1.38 | 2.76 | 0.68 | 1.38 | 2.76 | 1.38 |
| DHT-4A | | — | — | — | — | — | — | — | — | — | 1.38 |

TABLE 9

Physical Property Data

| | Comp TPV #13 | Comp TPV #14 | Comp TPV #15 | TPV #3 | TPV #4 | TPV #5 | TPV #6 | TPV #7 | TPV #8 | TPV #12 |
|---|---|---|---|---|---|---|---|---|---|---|
| Hardness (Shore A) | 67.4 | 67.0 | 70.9 | 69.8 | 68.3 | 70.0 | 70.6 | 71.9 | 71.0 | 71.2 |
| UTS(psi) | 966 | 894 | 1069 | 997 | 950 | 952 | 1011 | 1031 | 1051 | 1045 |
| UE(%) | 446 | 414 | 474 | 444 | 453 | 448 | 466 | 458 | 511 | 473 |
| M100(psi) | 370 | 359 | 421 | 400 | 363 | 386 | 392 | 407 | 382 | 396 |
| Weight Gain(%) | 96 | 84 | 99 | 93 | 104 | 97 | 97 | 93 | 99 | 96 |
| L | 81.98 | 81.41 | 81.35 | 83.40 | 84.60 | 84.66 | 84.42 | 84.50 | 84.34 | 83.93 |
| a | −0.58 | −0.65 | −0.84 | −1.09 | −1.29 | −1.21 | −1.33 | −1.46 | −1.57 | −1.34 |
| b | 5.83 | 6.15 | 5.95 | 4.62 | 4.36 | 4.52 | 5.00 | 5.14 | 5.20 | 5.57 |
| LCR(Pa · s) | 69.2 | 69.9 | 70.8 | 70.2 | 69.2 | 67.5 | 70.4 | 72.5 | 74.8 | 73.3 |
| Tension Set (%) | 15 | 15 | 15 | 15.5 | 17.0 | 12.5 | 12.5 | 12.5 | 12.5 | 12.5 |
| Compression Set at 100° C., 168 hr, (%) | 38 | 40 | 38 | 40 | 41 | 40 | 40 | 43 | 41 | 39 |

TABLE 10

Die Lip Buildup Data

| | Comp TPV #13 | Comp TPV #14 | Comp TPV #15 | TPV #3 | TPV #4 | TPV #5 | TPV #6 | TPV #7 | TPV #8 | TPV #12 |
|---|---|---|---|---|---|---|---|---|---|---|
| Time (min), visible die mustache buildup starts. | <1 | <1 | <5 | 10 | 5 | 5 | 5 | 5 | 5 | 5 |
| Time (min), mustache state dripping | <30 | <15 | None after 30 | None after 30 | None after 30 | None after 30 | None after 30 | None after 30 | None after 30 | None after 30 |
| Severity of Die Mustache at 30 min | Medium | Heavy | Medium | Little | Very Little | Medium | Little | Little | Medium | Little |

Thus, the features of the present invention can be described in one aspect as (1) a peroxide-cured thermoplastic vulcanizate composition comprising from 20 to 80% by weight of an at least partially cured elastomer and from 80 to 20% by weight of a thermoplastic; wherein the thermoplastic vulcanizate is cured in the presence of at least one multifunctional methacrylate coagent and at least one phosphorus containing stabilizer.

Other embodiments can be variously described in relation to the embodiment (1) above:

2. The thermoplastic vulcanizate of embodiment 1, wherein the thermoplastic vulcanizate is cured in the presence of from about 0.05 to about 12 phr of a multifunctional methacrylate coagent and from about 0.02 to about 8 phr of a phosphorus containing stabilizer.
3. The thermoplastic vulcanizate of any one of embodiments 1-2, wherein the phosphorus containing stabilizer is selected from the group consisting of phosphates, phosphonites and blends thereof.
4. The thermoplastic vulcanizate of any one of embodiments 1-3, wherein the multifunctional methacrylate coagent is trimetholpropane trimethacrylate.
5. The thermoplastic vulcanizate of any one of embodiments 1-4, wherein the elastomer is selected from the group consisting of ethylene/alpha-olefin elastomer, ethylene/alpha-olefin/non-conjugated diene elastomer, and blends thereof.
6. A method of forming a thermoplastic vulcanizate of any of the preceding embodiments 1-5, comprising the steps of melt blending from 20 to 80% by weight of at least one elastomer and from 80 to 20% by weight of a thermoplastic in the presence of a peroxide curing agent, a multifunctional methacrylate coagent and a phosphorus containing stabilizer.
7. The method of embodiment 6, wherein the melt blending takes place in a twin screw extruder.
8. The method of any one of embodiments 6-7, further comprising the step of extruding the melt-blended thermoplastic vulcanizate from the extruder.
9. The method of any one of embodiments 6-8, wherein the resulting melt-blended thermoplastic vulcanizate extrudate does not show die-lip buildup after 5 minutes.

The embodiments have been described, hereinabove. It will be apparent to those skilled in the art that the above

What we claim is:

1. A peroxide-cured thermoplastic vulcanizate composition comprising from 20 to 80% by weight of an at least partially cured ethylene-propylene-diene elastomer and from 80 to 20% by weight of a thermoplastic; wherein the thermoplastic vulcanizate is cured in the presence of from about 0.05 to about 12 parts by weight of trimetholpropane trimethacrylate per 100 parts by weight elastomer and from about 0.02 to about 6 parts by weight of bis(2,4-di-t-butylphenyl)pentaerythritol diphosphite per 100 parts by weight elastomer a phenolic stabilizer, and a synthetic hydrotalcite acid scavenger, where upon extrusion, the thermoplastic vulcanizate is characterized by forming an extrudate that does not show die-lip build up 5 minutes after the beginning of extrusion.

2. The thermoplastic vulcanizate of claim 1, further comprising an ultraviolet stabilizer, wherein the ultraviolet stabilizer is a hindered amine light stabilizer, selected from the group consisting of bis(2,2,6,6-tetramethyl-4-piperidinyl)sebacate, bis(1,2,2,6,6-pentamethyl-4-piperidinyl)sebacate, bis(1,2,2,6,6-pentamethyl-4-piperidinyl)2-n-butyl-(3,5-di-tert-butyl-hydroxy-benzyl)malonate, 8-acetyl-3-dodecyl-7,7,9,9-tetramethly-1,3,8-triazaspirol(4,5)decane-2,4-dione, tetra(2,2,6,6-tetramethyl-4-piperidinyl)-1,2,3,4-butanetetracarboxylate, 1-(-2-[3,5-di-tert -butyl-4-hydroxyphenyl-propionyloxyl]ethyl)-4-(3,5-di-tert-butyl-4-hydroxyphenylpropionyloxy)-2,2,6,6-tetramethylpiperidine, 1,1'-(1,2-ethenadiyl)bis(3,3,5,5-tetramethyl-2-piperazinone), 1,3,5-triazine-2,4,6-triamine,N,N'''-[1,2-ethanediylbis[[[4,6-bis(butyl(1,2,2,6,6-pentamethyl-4-piperidinyl)amino]-1,3,5-triazine-2-yl]imino]-3,1-propanediyl]]-bis[N',N''-dibutyl-N',N''-bis(1,2,2,6,6-entamethyl-4-piperidinyl), 7-oxa-3,20-diazadispiro[5.1.11.2]heneicosan-21-one-2,2,4,4-tetramethyl-20-oxiranylmethyl), homopolymer (9CI), and blends thereof.

3. The thermoplastic vuleanizate of claim 1, where the elastomer is cured in the presence of 1 to about 10 parts by weight of the trimetholpropane trimethacrylate per 100 parts by weight elastomer and in the presence of from about 0.2 to about 6 parts by weight of the bis(2,4-di-t-butylphenyl)pentaerythritol diphosphite per 100 parts by weight elastomer.

4. The thermoplastic vulcanizate of claim 1, where the elastomer is ethylene-propylene-diene including units deriving from 5-vinyl-2-norbornene.

5. The thermoplastic vulcanizate of claim 1, where the elastomer is cured to an extent that not more than 6 wt. % rubber is extractable by cyclohexane at 23° C.

6. The thermoplastic vulcanizate of claim 1, where upon extrusion, the thermoplastic vulcanizate is characterized by forming an extrudate that does not show dripping from die-lip buildup for 15 minutes from the beginning of extrusion.

7. A method for preparing a thermoplastic vulcanizate, the method comprising:
   i. preparing a molten blend by melt blending ingredients that include ethylene-propylene-diene elastomer, polypropylene, a peroxide, bis(2,4-di-t-butylphenyl)pentaerythritol diphosphite, a phenolic stabilizer, a synthetic hydrotalcite acid scavenger, and trimetholpropane trimethacrylate;
   ii. dynamically vulcanizing the elastomer in the presence of the polypropylene, the peroxide, the bis(2,4-di-t-butylpheny)pentaerythritol diphosphite, the phenolic stabilizer, the synthetic hydrotalcite acid scavenger, and the
   iii. extruding the thermoplastic vulcanite through a die to form an extrudate, wherein the resulting extrudate does not show die-lip buildup five minutes after the beginning of extrusion.

8. The method of claim 7, wherein the melt blending takes place in a twin screw extruder.

9. The method of claim 7, where the trimetholpropane trimethacrylate is provided to the blend together with a synthetic filler carrier.

10. The method of claim 9, where the elastomer is dynamically vulcanized in the presence of from about 0.05 to about 12 parts by weight of the trimetholpropane trimethacrylate per 100 parts by weight elastomer, in the presence of from about 0.02 to about 8 parts by weight of the bis(2,4-di-t-butylphenyl)pentaerythritol diphosphite per 100 parts by weight elastomer, in the presence of from about 0.05 to about 10 parts by weight of the peroxide per 100 parts by weight elastomer and in the presence of from about 0.01 to about 6 phr of the phenolic stabilizer.

11. The method of claim 7, where the ethylene-propylene-diene elastomer includes units deriving from 5-vinyl-2-norbornene.

12. The method of claim 7, where said step of dynamically vulcanizing cures the elastomer to an extent that not more than 6 wt. % of the elastomer is extractable by cyclohexane at 23° C.

13. The method of claim 7, where the resulting extrudate does not show dripping from die-lip buildup for 15 minutes from the beginning of extrusion.

* * * * *